(12) United States Patent
Nimura et al.

(10) Patent No.: US 7,935,249 B2
(45) Date of Patent: May 3, 2011

(54) BLOOD PURIFICATION APPARATUS AND METHOD FOR BLOOD PURIFICATION

(75) Inventors: Hiroshi Nimura, Makinohara (JP); Azusa Mori, Makinohara (JP); Yoshiro Ueda, Makinohara (JP)

(73) Assignee: Nikkiso Co., Ltd., Tokyo (JP)

( * ) Notice: Subject to any disclaimer, the term of this patent is extended or adjusted under 35 U.S.C. 154(b) by 292 days.

(21) Appl. No.: 11/391,164

(22) Filed: Mar. 27, 2006

(65) Prior Publication Data

US 2006/0213835 A1      Sep. 28, 2006

(30) Foreign Application Priority Data

Mar. 28, 2005   (JP) .................................. 2005-091983

(51) Int. Cl.
  *B01D 21/30*       (2006.01)
  *B01D 35/00*       (2006.01)
  *B01D 35/14*       (2006.01)
  *B01D 11/00*       (2006.01)

(52) U.S. Cl. ............ 210/143; 210/85; 210/87; 210/138; 210/645; 210/646; 210/739; 422/45; 604/4.01

(58) Field of Classification Search .................. 210/645, 210/646, 739, 85, 87, 97, 143; 604/4.01; 422/45

See application file for complete search history.

(56) References Cited

U.S. PATENT DOCUMENTS

| 5,382,227 A * | 1/1995 | Riquier ........................ 604/6.05 |
| 2002/0104800 A1* | 8/2002 | Collins et al. .................. 210/646 |
| 2003/0163077 A1* | 8/2003 | Kim et al. ..................... 604/5.01 |

FOREIGN PATENT DOCUMENTS

| JP | 2002-325837 A | 11/2002 | |
| JP | 2004-187990 A | 8/2004 | |
| WO | WO2007/113936 | * 10/2007 | .................... 210/646 |

OTHER PUBLICATIONS

Patent Abstracts of Japan for JP2002-325837 published Nov. 12, 2002.

* cited by examiner

*Primary Examiner* — Krishnan S Menon
*Assistant Examiner* — Dirk Bass
(74) *Attorney, Agent, or Firm* — McDermott Will & Emery LLP

(57) ABSTRACT

A blood purification apparatus includes a blood circuit, a blood purifying device, a first valve, a discharge line, a second valve, and a detection device. The blood circuit has an arterial blood circuit and a venous blood circuit. The first valve opens and closes the venous blood circuit. The second valve opens and closes the discharge line. The detection device detects whether a priming solution is replaced with blood in an end portion of the venous blood circuit at an upstream side from the first valve. The blood purification apparatus automatically turns the first valve from a closed position to an open position and the second valve from an open position to a closed position, respectively, when the detection device detects the priming solution being replaced with the blood.

5 Claims, 2 Drawing Sheets

Background Art

BLOOD PURIFICATION APPARATUS AND METHOD FOR BLOOD PURIFICATION

INCORPORATION BY REFERENCE

The present application claims priority under 35 U.S.C. §119 to Japanese Patent Application No. 2005-091983 filed on Mar. 28, 2005, the entire contents of which are incorporated herein by reference.

FIELD OF THE INVENTION

The present invention relates to a blood purification apparatus and method which purifies blood of a patient by circulating the blood extracorporeally.

BACKGROUND OF THE INVENTION

A dialysis machine in a conventional blood purification apparatus, as shown in FIG. 3, includes a blood circuit 100, a dialyzer 103, a blood pump 104, an arterial drip chamber 105, a venous drip chamber 106, an overflow line L2, and a dialysis device 108. The blood circuit 100 is provided with an arterial blood circuit 101 having an arterial needle a, and a venous blood circuit 102 having a venous needle b. The dialyzer 103 is provided between the arterial blood circuit 101 and the venous blood circuit 102, and purifies blood of a patient, flowing in the blood circuit 100. The arterial blood circuit 101 is provided with the blood pump 104. The arterial blood circuit 101 and the venous blood circuit 102 are each provided with the arterial drip chamber 105 and the venous drip chamber 106, respectively. The overflow line L2 is provided at an air-layer side of the venous drip chamber 105 and extended therefrom. The dialysis device 108 is capable of supplying dialysate to the dialyzer 103.

In addition, a saline solution bag 107 is connected to a portion of the arterial blood circuit 101 between the arterial needle a and the blood pump 104, and supplied with a priming solution (e.g., a saline solution) through a saline line L1 so as to perform priming prior to a dialysis treatment and supply an additional priming solution during the dialysis treatment. For example, when washing and priming are performed, an end of the arterial blood circuit 101 and an end of the venous blood circuit 102 are connected to each other before connecting each of the circuits 101 and 102 to the arterial needle a and the venous needle b, respectively. Subsequently, by turning on the blood pump 104, the blood circuit 100 is filled with the priming solution while discharging the priming solution from the overflow line L2.

To start the dialysis treatment, each of the arterial needle a and the venous needle b connected to each of the ends of the arterial blood circuit 101 and the venous blood circuit 102, respectively, is inserted into the patient. Then, by turning on the blood pump 104 while supplying the dialysate from the dialysis device 108 to the dialyzer 103, the blood of the patient is introduced to the blood circuit 100 through the arterial needle a to purify and remove water through the dialyzer 103, and returned to the patient through the venous needle b.

At the time the dialysis treatment is started, a large amount of the priming solution pre-filled in the blood circuit 100 is to be prevented from being introduced to the body of the patient through the venous needle b. Thus, conventionally, electromagnetic valves V1 and V2 are firstly set to closed and open positions, respectively, and switched to open and closed positions, respectively, when it is visually confirmed that the priming solution in a portion of the venous blood circuit 102 near the venous needle b is replaced with the blood.

Thus, by switching the positions of the electromagnetic valves V1 and V2, the priming solution is discharged from the overflow line L2 prior to being replaced with the blood in the portion of the venous blood circuit 102 near the venous needle b, and the blood is returned to the body of the patient through the venous blood needle b after replacing the priming solution. For example, the above-described conventional blood purification apparatus, which discharges the priming solution from the overflow line L2 and replaces the priming solution with the blood, is described in the Japanese Laid-Open Patent Publication 2002-325837.

However, when using such conventional blood purification apparatus, because the electromagnetic valves V1 and V2 are manually switched in positions after a medical staff (e.g., a medical doctor) visually confirms that the priming solution in the portion of the venous blood circuit 102 near the venous needle b is replaced with the blood, the medical staff has to carefully monitor that portion of the venous blood circuit 102 at the time the dialysis treatment is started, making the dialysis treatment inefficient. Also, if the electromagnetic valves V1 and V2 are switched in positions too early, a large amount of the priming solution is introduced to the body of the patient. On the other hand, if switched too late, the patient's blood circulated extracorporeally is discharged from the overflow line L2.

SUMMARY OF THE INVENTION

The object of the present invention is to provide a blood purification apparatus and a method for blood purification to perform an efficient blood purification treatment at the time the treatment is started, to prevent the large amount of the priming solution from being introduced to the body of the patient, and to efficiently return the blood to the patient after extracorporeally circulating the blood.

According to one aspect of the present invention, a blood purification apparatus includes a blood circuit, a blood purifying device, a first valve, a discharge line, a second valve, and a detection device. The blood circuit is filled with a priming solution, and has an arterial blood circuit and a venous blood circuit. The blood circuit allows blood of a patient to circulate extracorporeally from an end of the arterial blood circuit to an end of the venous blood circuit. The blood purifying device is provided between the arterial blood circuit and the venous blood circuit, and purifies the blood flowing in the blood circuit. The first valve opens and closes the venous blood circuit, and allows and prevents a flow of the priming solution and the blood, flowing from the end of the venous blood circuit into the patient. The discharge line extends from the blood circuit at an upstream side from the first valve, and discharges the priming solution flowing in the blood circuit. The second valve opens and closes the discharge line, which allows and prevents a flow of the priming solution and the blood that is flowing in the discharge line. The detection device detects whether the priming solution is replaced with blood in an end portion of the venous blood circuit at the upstream side from the first valve. The blood purification apparatus automatically turns the first valve from a closed position to an open position and the second valve from an open position to a closed position, respectively, when the detection device detects the priming solution being replaced with the blood.

According to another aspect of the present invention, a method for blood purification uses a blood purification apparatus including a blood purifying device provided along a blood circuit between an arterial blood circuit and a venous blood circuit. The method includes filling a priming solution into the blood circuit from an end of the arterial blood circuit to an end of the venous blood circuit. The priming solution is prevented from flowing to the end of the venous blood circuit when the priming solution is flowing in an end portion of the venous blood circuit. The priming solution is discharged through a discharge line extending from the blood circuit at an upstream side from a first valve. A detection device detects when the priming solution is to be replaced with the blood in the end portion of the venous blood circuit. The discharge of blood through the discharge line is prevented when the priming solution is detected to be replaced with blood. The blood is automatically allowed to flow to the end of the venous blood circuit.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE INVENTION

Figure 1:
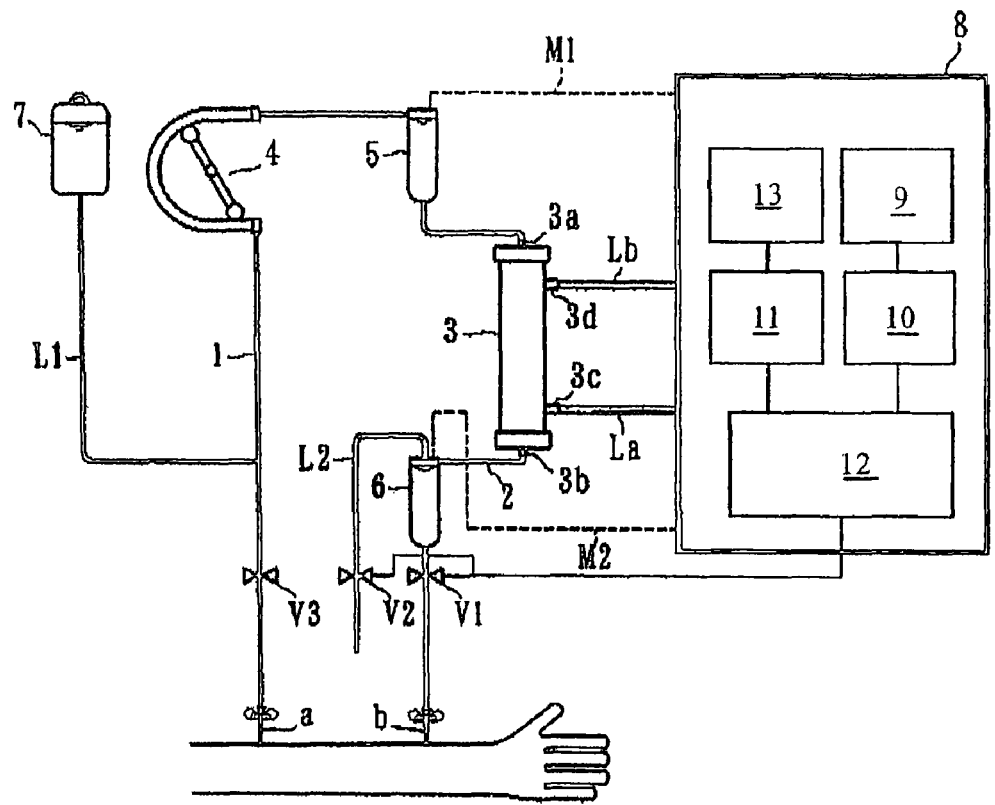
FIG. 1 is a schematic diagram of a blood purification apparatus of the present invention.

The embodiments will now be described with reference to the accompanying drawings, wherein like reference numerals designate corresponding or identical elements throughout the various drawings.

FIG. 1 is a schematic diagram of a blood purification apparatus of the present invention. Referring to FIG. 1, a blood purification apparatus is provided with a dialysis machine including a blood circuit, a dialyzer 3, a blood pump 4 and a dialysis device 8. The blood circuit has an arterial blood circuit 1 and a venous blood circuit 2, each provided with an arterial drip chamber 5 and a venous drip chamber 6, respectively. The venous drip chamber 6 is provided with an overflow line L2 extended from an air-layer side of the venous drip chamber 6. For a blood purifying device to purify blood flowing in the blood circuit, the dialyzer 3 is provided between the arterial blood circuit 1 and the venous blood circuit 2. A dialysis device 8 supplies dialysate to the dialyzer 3.

The arterial blood circuit 1 is provided with an arterial needle a that is connected to an end thereof, the blood pump 4 (e.g., a roller-type pump) and the arterial drip chamber 5 to remove air-bubbles. The venous blood circuit 2 is provided with a venous needle b that is connected to an end thereof, and the venous drip chamber 6. When the blood pump 4 is turned on while the arterial needle a and the venous needle b are inserted to the body of a patient, the blood of the patient flows through the arterial blood circuit 1 into the dialyzer 3 that purifies the blood. Then, the blood returns into the body of the patient through the venous blood circuit 2 after air-bubbles in the blood are removed in the venous drip chamber 6. Thus, the blood of the patient is purified by the dialyzer 3 during extracorporeal circulation from the end of the arterial blood circuit 1 to the end of the venous blood circuit 2.

The dialyzer 3 is provided with a blood inlet port 3a, a blood outlet port 3b, a dialysate inlet port 3c and a dialysate outlet port 3d. The blood inlet port 3a is connected to the arterial blood circuit 1, and the blood outlet port 3b is connected to the venous blood circuit 2. Further, the dialysate inlet port 3c and the dialysate outlet port 3d are each connected to a dialysate inlet line La and a dialysate outlet line Lb, respectively, which are extended from the dialysis device 8.

The dialyzer 3 includes a plurality of hollow fibers. The blood flows the inside of the hollow fibers, and the dialysate flows between an outside surface of the hollow fibers and an inside surface of a case of the dialyzer 3. The hollow fibers are provided with a plurality of micropores on the inside and outside surfaces of the hollow fibers. This forms permeable membranes which allow waste products in the blood to permeate into the dialysate.

The dialysis device 8 is provided with a water removal pump (not shown) to remove water from the blood of the patient flowing in the inside of the dialyzer 3. Additionally, one end of the dialysate inlet line La is connected to the dialyzer 3 at the dialysate inlet port 3c, and another end thereof is connected to a dialysate supplying device (not shown) that adjusts the dialysate to a predetermined concentration. Also, one end of the dialysate outlet line Lb is connected to the dialyzer 3 at the dialysate outlet port 3d, and another end is connected to a fluid disposal device (not shown). The dialysate supplied from the dialysis supplying device flows through the dialysate inlet line La into the dialyzer 3, then, through the dialysate outlet line Lb, flows into the fluid disposal device.

In addition, the arterial drip chamber 5 and the venous drip chamber 6 are provided with monitor tubes M1 and M2, respectively, ends of which are connected to the dialysis device 8. The dialysis device 8 includes a pressure sensor 9 which measures by the monitor tubes M1 and M2 a liquid pressure in the arterial drip chamber 5 (a dialyzer inlet blood pressure) and a liquid pressure in the venous drip chamber 6 (a venous blood pressure), respectively.

Further, a third electromagnetic valve V3 (e.g., a solenoid valve) is provided at an end portion of the arterial blood circuit 1 near the arterial needle a (i.e., between points along the arterial blood circuit 1, where a saline line L1 is connected and where the arterial needle a are provided). A first electromagnetic valve V1 (e.g., a solenoid valve) is provided at an end portion of the venous blood circuit 2 near the venous needle b (i.e., between the venous drip chamber 6 and the venous needle b along the venous blood circuit 2). The first electromagnetic valve V1 is capable of opening and closing the venous blood circuit 2 at the end portion near the venous needle b to allow and prevent the priming solution and the blood from flowing into the patient through the venous needle b.

Furthermore, the saline line L1 is extended from a portion of the arterial blood circuit 1 between arterial needle a and the blood pump 4, and connected to a saline solution bag 7 supplied with the priming solution (e.g. a saline solution). An overflow line L2 is extended from an air-layer side (i.e., an upper portion) of the venous drip chamber 6, and provided with a second electromagnetic valve V2 (e.g., a solenoid valve) capable of opening and closing the overflow line L2 to allow and prevent flows of the priming solution and the blood.

When washing and priming are performed prior to the dialysis treatment, an end of the arterial blood circuit 1 and an end of the venous blood circuit 2 are connected to each other before the arterial needle a and the venous needle b are inserted into the patient. Then, the first, second and third electromagnetic valves V1, V2 and V3 are each switched to an open position. Subsequently, the blood pump 4 is tuned on, the priming solution in the saline solution bag 7 is then introduced into the blood circuit, and a portion of the priming solution overflowed from the venous drip chamber 6 is discharged from the overflow line L2. Accordingly, the blood circuit is filled with the priming solution. When the priming is finished, the electromagnetic valves V1 and V3 are switched to a closed position, and the saline line L1 is in a closed position by being clamped.

At the time the dialysis treatment is started, the arterial needle a and the venous needle b are each connected to the end of the arterial blood circuit 1 and the end of the venous blood circuit 2, respectively. Then, after those needles a and b are inserted into the patient, the dialysate is supplied from the dialysis device 8 to the dialyzer 3, and the blood pump 4 is turned on to introduce the blood of the patient into the blood circuit through the arterial needle a. Immediately after the dialysis treatment is started, the first electromagnetic valve V1 is in the closed position, and the second and third electromagnetic valves V2 and V3 are in the open position. The pre-filled priming solution is discharged from the overflow line L2 during the process of replacing the priming solution with the blood in an upstream side of the blood circuit.

Moreover, the dialysis device 8 is provided with a differential pressure calculation device 10, a timer 11 and a switching control device 12. The differential pressure calculation device 10 is electrically connected to the pressure sensor 9. The timer 11 measures an elapsed time from the start of the dialysis treatment (i.e., the start of the extracorporeal circulation of the blood of the patient). The switching control device 12 is electrically connected to the differential pressure calculation device 10 and the timer 11. The differential pressure calculation device 10 and the timer 11 together form a detection device.

Figure 2:
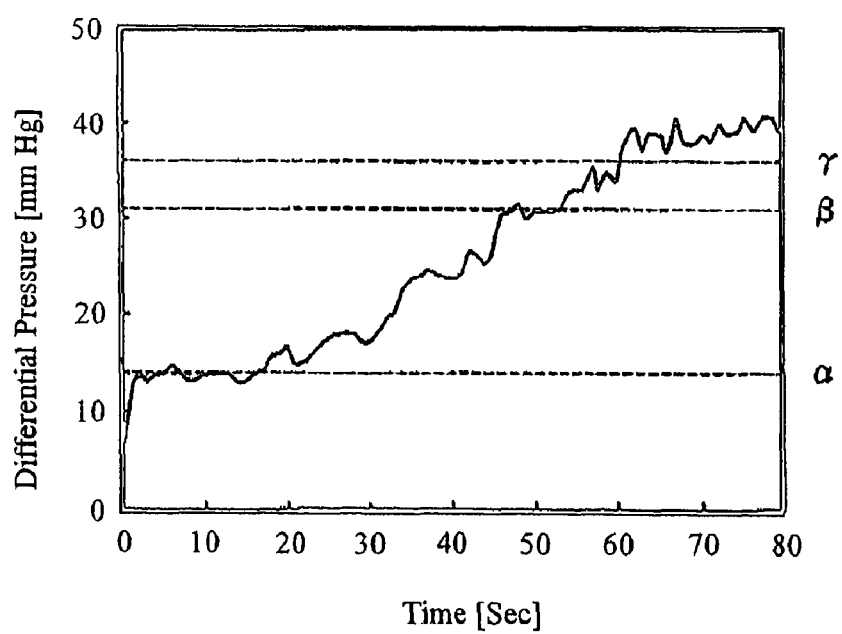
FIG. 2 is a graph having a longitudinal axis showing a differential pressure calculated by a differential pressure calculation device, and a horizontal axis showing elapsed time from the time a dialysis treatment is started.
Figure 3:
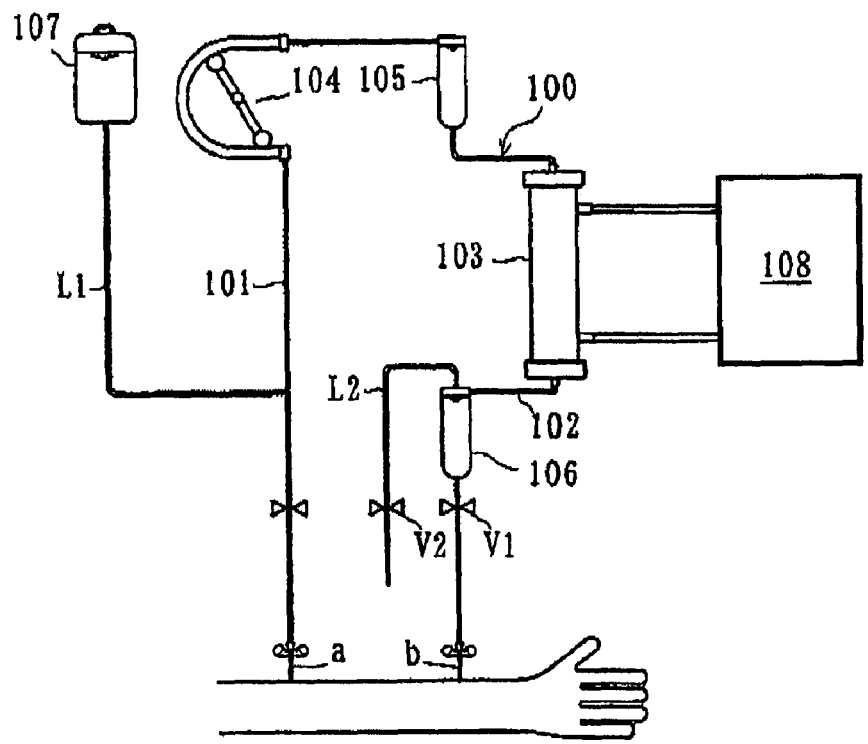
FIG. 3 is a schematic diagram of a blood purification apparatus of background art.

The differential pressure calculation device 10 calculates a differential pressure that is the difference between a liquid pressure of the inside of the arterial drip chamber 5 and a liquid pressure of the inside of the venous drip chamber 6. For example, if conditions are such that a membrane area of dialyzer 3 is 1.5 m$^2$; the inner diameter of the hollow fiber is 210 µm; a capacity (an amount of the blood filled) is 91 mL; the inner diameter of tubes of the blood circuit is 3.4 mm; a capacity of the arterial blood circuit 1 is 63 mL; a capacity of the venous blood circuit 2 is 64 mL; a temperature of the blood is 37° C.; a hematocrit is 32%; and a flow rate is 100 mL/min, it is found that a resultant differential pressure gradually increases as time elapses as shown in the graph of FIG. 2.

Specifically, because the viscosity of the blood is higher than the priming solution, the differential pressure obtained by the differential pressure calculation device 10 has a low value while the priming solution is flowing in the inside of the dialyzer 3, and becomes a higher value due to tubing resistance as the blood starts flowing in the inside of the dialyzer 3 after the priming solution is replaced by the blood. For example, the following data is obtained as references in advance when the replacement of the priming solution with the blood is performed: the differential pressure α mmHg at the time the blood flows into the upstream side of the dialyzer 3, the differential pressure β mmHg at the time the blood flows into the downstream side of the dialyzer 3, and the differential pressure γ mmHg at the time the blood is discharged from the overflow line L2. Referring to the above data, when the differential pressure calculation device 10 detects the differential pressure reaching β mmHg, the replacement of the priming solution with the blood in the end portion of the venous blood circuit near the venous needle b (i.e., near the end of the venous blood circuit 2 and the upstream side of the first electromagnetic valve V1) is detected.

The switching control device 12 is electrically connected to the first and second electromagnetic valves V1 and V2, and switches the valves V1 and V2 to the open and closed positions. When the differential pressure obtained by the differential pressure calculation device 10 reaches to β mmHg, the switching control device 12 automatically switches the second electromagnetic valve V2 from the open position to the closed position, and the first electromagnetic valve V1 from the closed position to the open position. By this switching, the discharge from the overflow line L2 is prevented, and the blood circulated extracorporeally returns to the patient through the venous needle b.

Accordingly, in contrast to the conventional blood purification apparatus in which the first and second electromagnetic valves V1 and V2 are manually switched by visually confirming the priming solution being replaced with the blood in the end portion of the venous blood circuit 2 near the venous needle b at the start of the dialysis treatment, the above-described embodiment of the present invention makes the dialysis treatment efficient, and makes the blood circulated extracorporeally return efficiently to the patient without introducing a large amount of the priming solution into the patient. Further, according to this embodiment of the present invention, because the replacement of the priming solution with the blood is detected in reference to the differential pressure calculated based on the liquid pressures of the arterial and venous drip chambers 5 and 6, which are measured by the pressure sensor 9 in the dialysis device 8, manufacturing costs of the blood purification apparatus is reduced.

Additionally, the blood purification apparatus according to the present invention may include an alarm system 13 which warns that the blood is discharged from the overflow line L2 when the differential pressure obtained by the differential pressure calculation device 10 reaches to γ mmHg, The alarm system 13 may be any alarm device including an audible alert with a speaker, a display device that displays alerting messages or a remote device that activates a pager or a cellular device. In addition, the graph shown in FIG. 2 may be displayed to have a medical staff visually recognize changes in the differential pressure.

The timer 11 measures, as described above, the elapsed time from the start of the dialysis treatment (i.e. the start of the extracorporeal circulation of the blood of the patient). By obtaining in advance a period of time (a switching time) until the blood reaches to the upstream side of the dialyzer 3 by the replacement of the priming solution with the blood, the timer 11 transmits to the switching control device 12 a signal indicating that the switching time is passed, and, then, the switching control device 12 automatically turns the second electromagnetic valve V2 from the open position to the closed position and the first electromagnetic valve V1 from the closed position to the open position.

Accordingly, when the differential pressure calculation device 10 does not properly perform the detection due to either or both mechanical and electrical problems, the timer 11 forces the first and second electromagnetic valves V1 and V2 to be switched in the positions. Thus, the timer 11 functions as a fail-safe device.

A method for blood purification using the above-described blood purification apparatus of the present invention is described below.

The arterial needle a and the venous needle b are each connected to the ends of the arterial blood circuit 1 and the venous blood circuit 2, respectively, of the blood circuit filled with the priming solution, and, then, the needles a and b are inserted into the patient. At this point, the first electromagnetic valve V1 is in the closed position, and the second and third electromagnetic valves V2 and V3 are in the open position. Also, the saline line L1 is in the closed position by being clamped.

The blood pump 4 is then turned on to start the dialysis treatment. At this point, the blood of the patient starts replacing the priming solution from the upstream side of the blood circuit and flows toward the downstream side of the blood circuit. The dialyzer 3 removes water and purifies the blood. The pre-filled priming solution overflows in the venous drip chamber 6 and is discharged through the overflow line L2.

The pressure sensor 9 measures in real-time the liquid pressures of the arterial and venous drip chambers 5 and 6. The differential pressure calculation device 10 calculates the differential pressure based on the liquid pressures of the arterial and venous drip chambers 5 and 6. When the differential pressure reaches β mmHg, the switching control device 12 automatically switches the second electromagnetic valve V2 from the open position to the closed position and the first electromagnetic valve V1 from the closed position to the open position.

Thus, when the priming solution is flowing in the portion of the venous blood circuit near the venous needle b, the priming solution is prevented to flow toward the venous needle b, and is discharged through the overflow line L2. Then, when the differential pressure calculation device 10 detects that the priming solution in the end portion of the venous blood circuit near the venous needle b is replaced with blood, the discharge through the overflow line L2 is prevented, and the flow to the venous needle b is opened by automatically switching the first and second electromagnetic valves V1 and V2.

According to the above embodiment of the present invention, because the overflow line L2, which is required in performing the priming, is also utilized in the dialysis treatment (a blood purification treatment), manufacturing costs of the blood purification apparatus is reduced. Further, the overflow line L2 may be replaced by another discharge line extended from the upstream side of the first electromagnetic valve V1 along the blood circuit. The other discharge line may also be used to discharge the priming solution flowing in the blood circuit.

The present invention is not limited to the above-described embodiments. For example, in another embodiment, the switching control device 12 may switch the first and second electromagnetic valves V1 and V2 primarily based on the elapsed time measured by the timer 11. According to such embodiment, because the blood purification apparatus has a simple structure that efficiently detects the priming solution being replaced with the blood, manufacturing costs of the blood purification apparatus is reduced.

Further, according to another embodiment, another detection device including a blood distinguishing unit may be used. In such embodiment, the blood distinguishing unit is provided at the downstream side of the dialyzer 3 along the blood circuit, and the switching control device 12 automatically switches the second electromagnetic valve V2 from the open position to the closed position and the first electromagnetic valve V1 from the closed position to the open position, when the blood distinguishing unit detects the blood by distinguishing the blood from the priming solution.

In such embodiment, the blood distinguishing unit is positioned either one of between the dialyzer 3 and the venous drip chamber 6 along the venous blood circuit 2, at the venous drip chamber 6, or along the overflow line L2. If the blood distinguishing device is positioned between the dialyzer 3 and the venous drip chamber 6, an amount of the priming solution introduced into the body of the patient increases relative to the other two positions. However, in such positioning of the blood distinguishing unit, because the blood does not flow into the overflow line L2, there is no loss of the blood. Alternatively, if the blood distinguishing device is positioned along the overflow line L2, there is a small amount of loss of the blood because the blood flows into the overflow line L2. In addition, such positioning of the blood distinguishing unit decreases the amount of the priming solution introduced into the body of the patient although it may cause a blood clot due to stagnation of the blood during the dialysis treatment.

Furthermore, although the present invention is applied in the above-described embodiments to the dialysis machine utilized in the dialysis treatment, it may be applied to other machines in the blood purification apparatus, which purify the blood by extracorporeal circulation (e.g., machines in hemodiafiltration, hemofiltration, machines used for AFBF, and blood plasma absorption machines).

Moreover, the present invention may be applied to other machines in the blood purification apparatus and methods, including a machine and a method which prevent the priming solution from flowing into the end of the venous blood circuit and discharge the priming solution through the discharge line extending from the end portion of the venous blood circuit, when the priming solution is flowing in the end portion of the venous blood circuit; and automatically switch flows to prevent the discharge from the discharge line and to allow the flow to the end of the venous blood circuit, when the detection device detects the priming solution in the end portion of the venous blood circuit being replaced with the blood.

Obviously, numerous modifications and variations of the present invention are possible in light of the above teachings. It is therefore to be understood that within the scope of the appended claims, the invention may be practiced otherwise than as specifically described herein.

What is claimed is:

1. A blood purification apparatus comprising:
   a blood circuit filled with a priming solution, having an arterial blood circuit and a venous blood circuit, the blood circuit allowing blood of a patient to circulate extracorporeally from an end of the arterial blood circuit to an end of the venous blood circuit;
   a blood purifying device provided between the arterial blood circuit and the venous blood circuit of the blood circuit and configured to purify the blood flowing in the blood circuit;
   a first valve configured to open and close the venous blood circuit, and to allow and prevent a flow of the priming solution and the blood, flowing from the end of the venous blood circuit into the patient;
   a discharge line extending from the blood circuit at an upstream side from the first valve, and configured to discharge the priming solution flowing in the blood circuit;
   a second valve configured to open and close the discharge line, and to allow and prevent a flow of the priming solution and the blood, flowing in the discharge line;
   a calculation device configured to calculate a differential pressure between a liquid pressure in an arterial drip chamber and a liquid pressure in a venous drip chamber; and
   a detection device configured to detect whether the priming solution is replaced with the blood in an end portion of the venous blood circuit at the upstream side from the first valve based on the differential pressure, the blood purification apparatus being configured to automatically turn the first valve from a closed position to an open position and the second valve from an open position to a closed position, respectively, when the detection device detects the priming solution being replaced with the blood.

2. The blood purification apparatus according to claim 1, wherein:
   the arterial blood circuit is provided with the arterial drip chamber to remove bubbles in the priming solution and the blood;
   the venous blood circuit is provided with the venous drip chamber to remove bubbles in the priming solution and the blood; and
   the discharge line is an overflow line extending from an air-layer side of the venous drip chamber.

3. The blood purification apparatus according to claim 1, further comprising:
   a timer configured to measure an elapsed time from a start of extracorporeal circulation of the blood, wherein the detection device detects whether the priming solution is replaced with the blood, based on the elapsed time measured by the timer.

4. The blood purification apparatus according to claim 2, further comprising:
   a timer configured to measure an elapsed time from a start of extracorporeal circulation of the blood, wherein the detection device detects whether the priming solution is replaced with the blood, based on the elapsed time measured by the timer.

5. The blood purification apparatus according to claim 1, further comprising an alarm, wherein:
   the detection device detects a presence of the blood in the discharge line; and
   the alarm indicates the presence of the blood.

* * * * *